United States Patent
Uhr et al.

(10) Patent No.: US 9,951,205 B2
(45) Date of Patent: *Apr. 24, 2018

(54) STABLE COMPOSITIONS OF THIABENDAZOLE AND IODINE-CONTAINING FUNGICIDES

(71) Applicant: LANXESS Deutschland GmbH, Cologne (DE)

(72) Inventors: Hermann Uhr, Leverkusen (DE); Andreas Boettcher, Cologne (DE); Thomas Jaetsch, Cologne (DE)

(*) Notice: Subject to any disclaimer, the term of this patent is extended or adjusted under 35 U.S.C. 154(b) by 146 days.

This patent is subject to a terminal disclaimer.

(21) Appl. No.: 14/385,809

(22) PCT Filed: Mar. 26, 2013

(86) PCT No.: PCT/EP2013/056402
§ 371 (c)(1),
(2) Date: Sep. 17, 2014

(87) PCT Pub. No.: WO2013/144145
PCT Pub. Date: Oct. 3, 2013

(65) Prior Publication Data
US 2015/0051279 A1    Feb. 19, 2015

(30) Foreign Application Priority Data

Mar. 28, 2012 (EP) .................. 12161923
Apr. 23, 2012 (EP) .................. 12165125

(51) Int. Cl.
| | | |
|---|---|---|
| *A01N 47/12* | (2006.01) |
| *C08K 5/47* | (2006.01) |
| *C08L 27/06* | (2006.01) |
| *C08K 5/00* | (2006.01) |
| *C08K 5/205* | (2006.01) |
| *C09D 5/14* | (2006.01) |
| *C09D 127/06* | (2006.01) |
| *C08K 5/12* | (2006.01) |
| *C08K 5/1515* | (2006.01) |

(52) U.S. Cl.
CPC .............. *C08K 5/47* (2013.01); *A01N 47/12* (2013.01); *C08K 5/0016* (2013.01); *C08K 5/0058* (2013.01); *C08K 5/12* (2013.01); *C08K 5/1515* (2013.01); *C08K 5/205* (2013.01); *C09D 5/14* (2013.01); *C09D 127/06* (2013.01)

(58) Field of Classification Search
None
See application file for complete search history.

(56) References Cited

U.S. PATENT DOCUMENTS

| | | |
|---|---|---|
| 4,276,211 A | 6/1981 | Singer et al. |
| 4,297,258 A | 10/1981 | Long, Jr. |
| 4,552,885 A | 11/1985 | Gabriele et al. |
| 5,366,995 A | 11/1994 | Savage et al. |
| 5,955,483 A | 9/1999 | Gaglani et al. |
| 6,136,856 A | 10/2000 | Savage et al. |
| 6,140,370 A | 10/2000 | Gaglani et al. |
| 6,353,021 B1 | 3/2002 | Gaglani et al. |
| 6,472,424 B1 | 10/2002 | Gaglani et al. |
| 7,348,380 B2 | 3/2008 | Koube et al. |
| 8,036,862 B2 | 10/2011 | Funk |
| 9,328,065 B2 | 5/2016 | Bottcher et al. |
| 2009/0036555 A1 | 2/2009 | Uhr |
| 2010/0330185 A1 | 12/2010 | Boettcher et al. |
| 2012/0186487 A1 | 7/2012 | Bottcher |
| 2013/0096227 A1 | 4/2013 | Cornish et al. |
| 2013/0310428 A1 | 11/2013 | Joseph et al. |

FOREIGN PATENT DOCUMENTS

| | | |
|---|---|---|
| GB | 002712055 A1 | 2/2011 |
| JP | 53139657 A2 | 12/1978 |
| JP | 6313269 A2 | 11/1994 |
| JP | 7041409 A2 | 2/1995 |
| JP | 10120515 A2 | 5/1998 |
| JP | 02225548 A2 | 8/2002 |
| JP | 2003104801 A2 | 4/2003 |
| JP | 2004231872 A2 | 8/2004 |
| JP | 08059937 A2 | 3/2008 |
| WO | 12032206 A1 | 3/2012 |

OTHER PUBLICATIONS

Dylingowski, P, Directory of microbicides for the protection of materials; Springer 2005, pp. 325-345; ISBN 1-4020-2817-2.
ISR from corresponding application PCT/EP2013/056402, dated Sep. 10, 2013 (2 pages).

*Primary Examiner* — Alton N Pryor

(57) ABSTRACT

The present invention relates to stable compositions for the fungicidal equipment of thermoplastic polymers, in particular PVC, comprising thiabendazole, at least one iodine-containing fungicide and at least one epoxide and optionally further fungicidally active compounds, and also to methods for preparing these formulations and to uses thereof for the protection of thermoplastic polymers against attack and destruction by microorganisms. Moreover, the invention relates to mold-resistant PVC materials equipped with the compositions according to the invention.

14 Claims, No Drawings

STABLE COMPOSITIONS OF THIABENDAZOLE AND IODINE-CONTAINING FUNGICIDES

The present invention relates to stable compositions for the fungicidal equipment of thermoplastic polymers, in particular PVC, comprising thiabendazole, at least one iodine-containing fungicide and at least one epoxide and optionally further fungicidally active compounds, and also to methods for preparing these formulations and to uses thereof for the protection of thermoplastic polymers against attack and destruction by microorganisms. Moreover, the invention relates to mold-resistant PVC materials equipped with the compositions according to the invention.

Since the first synthetic polymers were introduced in the 19th century, attack and degradation of polymers by microorganisms such as, for example, fungi plays a major role. The tendency to be attacked and possibly decomposed by microorganisms depends strongly on the structure of the polymers and the additives used. Flexible polyvinyl chloride, which is used, for example, for films for swimming pools, ponds and reservoirs, for textiles, shower curtains, floor seals, floor pads and floor covers, seat covers, flexible seals for refrigerators and washing machines, seals used for roofing, etc., is particularly susceptible to attack by microorganisms owing to its high proportion of plasticizers and other additives. For protection against microorganisms, soft PVC is therefore equipped with antimicrobial agents. Currently, a large proportion is still equipped with the toxicologically highly questionable 10'-oxybisphenoxyarsine (OBPA). As alternatives, use is increasingly made of 2-n-octyl-4-isothiazolin-3-one (OIT) or 4,5-dichloro-2-n-octyl-4-isothiazolin-3-one (DCOIT); however, owing to their highly sensitizing properties they are also fraught with problems. (W. Paulus, Directory of microbicides for the protection of materials; Springer 2005, pp. 325 345; ISBN 1-4020-2817-2).

By virtue of its favorable toxicological properties, thiabendazole is an ideal fungicide for equipping plastics such as, for example, PVC.

The use of thiabendazole and compositions of thiabendazole with other fungicides for antifungal equipment of soft PVC have already been described in numerous patent applications and publications.

JP 08059937 describes antibacterially and antifungally equipped PVC films comprising, for example, thiabendazole as fungicidally active compound.

JP 02225548 claims thiazolyl derivatives including thiabendazole for protecting vinyl chloride polymers against mold.

Borgmann-Strahsen, R.; Bessems, E. Kunststoffe 84 (1994) 158-162 describes compositions of thiabendazole and n-octylisothiazolinone ensuring good protection of PVC against attack by mold.

WO 2008075014 describes antifungal formulations comprising a plasticizer, and articles prepared from or coated with these compositions. The fungicides are fludioxonil and/or difenoconazole, with thiabendazole also being mentioned as optional mixing partner.

DE 10146189 claims mold-free PVC compositions for refrigerator door seals, which compositions comprise, as fungicidal component, carbendazim, thiabendazole, tebuconazole or zinc pyrithione.

Suitable further additives are iodine-containing fungicides, which supplement the activity spectrum of thiabendazole.

Powder mixtures of thiabendazole and iodine-containing fungicides, in particular in combination with iodopropargyl butylcarbamate, are already available as fungicidal mixtures for plastics; however, for toxicological and safety reasons, their handling is disadvantageous.

Mixtures of thiabendazole and plasticizers are frequently suspensions or dispersions in which thiabendazole is, if at all, only poorly soluble in conventional plasticizers. In these suspensions, thiabendazole tends to agglomeration and sedimentation. As a result, corresponding compositions can no longer be uniformly incorporated into a polymer without further technical expenditure.

Furthermore, mixtures of thiabendazole and iodine-containing fungicides in plasticizers tend to decompose since in particular dispersions or suspensions of thiabendazole and iodine-containing fungicides are unstable, especially at elevated temperatures. The iodine-containing fungicides are then chemically degraded even after a relatively short period of time.

Methods for preventing the degradation of iodopropargyl compounds in transition metal-containing solvent-based alkyd resin-containing paints and for stabilizing them in this manner are known in the state of the art. Here, the presence of transition metals is causing the decomposition of the iodopropargyl compounds. Thus, it is known to add, for example, chelating agents (WO 98/22543 A), organic epoxides (WO 00/16628 A, 2-(2-hydroxyphenyl)benzotriazoles (WO 2007/028527 A) or azole compounds (WO 2007/101549 A).

Also known are methods for reducing the light-induced discoloration of iodopropargyl compounds in water-based paints by employing epoxides (U.S. Pat. No. 4,276,211, U.S. Pat. No. 4,297,258), optionally in combination with UV absorbers (WO 99/29176 A) or benzylidene camphor derivatives (U.S. Pat. No. 6,472,424), tetraalkylpiperidine compounds and/or UV absorbers (EP 0 083 308 A).

The decomposition of the iodine-containing fungicides in the presence of thiabendazole in dispersions is different from the decomposition induced by transition metals or light. In the presence of thiabendazole, the active compound thiabendazole causes the decomposition of the iodine-containing fungicides.

Accordingly, it was an object of the present invention to prepare a sedimentation- and storage-stable formulation of thiabendazole and iodine-containing fungicides in plasticizers.

This object is advantageously achieved by a composition comprising thiabendazole, its salts or acid addition compounds, at least one iodine-containing fungicide and at least one epoxide.

Accordingly, the invention provides compositions comprising thiabendazole, its salts or acid addition compounds, at least one iodine-containing fungicide and at least one epoxide.

For the purpose of the invention, compositions are mixtures which may be present in various states. The compositions according to the invention are preferably dispersions.

In general, the epoxides employed can be any compounds containing one or more epoxide groups in the molecule and otherwise compatible with thiabendazole, the iodine-containing fungicides and auxiliaries and having a boiling point above the processing temperature of the PVC. Hereinbelow, compounds containing one or more epoxide groups in the molecule are referred to as "epoxides". The epoxides which can be employed as stabilizers in the context of the invention generally have a boiling point above 180° C. and preferably a boiling point above 200° C.

The epoxides which may preferably be used include the following compounds:

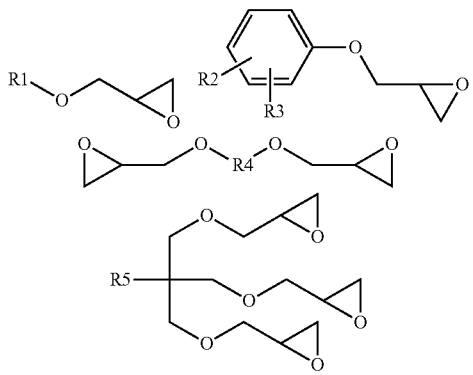

where
R$^1$ represents C$_1$-C$_{20}$-alkyl
R$^2$ represents H, alkyl, substituted alkyl,
R$^3$ represents halogen,
R$^4$ represents C$_1$-C$_{20}$-alkyl and
R$^5$ represents H, C$_1$-C$_{20}$-alkyl, preferably methyl or ethyl,
and preferably epoxides such as
1-methyl-4-(1-methylethenyl)-7-oxabicyclo[4.1.0]heptane (CAS-RN 1195-92-2), 1-methyl-4-(2-methyl-2-oxiranyl)-7-oxabicyclo[4.1.0]heptane (CAS-RN 96-08-2), 2,2'-[1,4-cyclohexanediylbis(methyleneoxymethylene)]bis-oxirane (CAS-RN 14228-35-5), 2,2'-[(1-methylethylidene)bis(4,1-phenyleneoxymethylene)]bis-oxirane (CAS-RN 1675-54-3), 3-(2-oxiranyl)-7-oxabicyclo[4.1.0]heptane (CAS-RN 106-87-6), 7-oxabicyclo[4.1.0]hept-3-ylmethyl-7-oxabicyclo[4.1.0]heptane-3-carboxylic acid ester (CAS-RN 2386-87-0), 1,6-bis(7-oxabicyclo[4.1.0]hept-3-ylmethyl)-hexanedioic acid ester (CAS-RN 3130-19-6), and also further epoxides prepared by epoxidation of double bonds in unsaturated fatty acids, fatty acid esters and fatty acid glycerides. Suitable for use as epoxidized fatty acids are preferably the epoxides of monounsaturated fatty acids such as (10Z)-undeca-10-enoic acid, (9Z)-tetradeca-9-enoic acid, (9Z)-hexadeca-9-enoic acid, (6Z)-octadeca-6-enoic acid, (9Z)-octadeca-9-enoic acid, (9E)-octadeca-9-enoic acid, (11E)-octadeca-11-enoic acid, (9Z)-eicosa-9-enoic acid, (11Z)-eicosa-11-enoic acid, (11Z)-docosa-11-enoic acid, (13Z)-docosa-13-enoic acid or (15Z)-tetracosa-15-enoic acid, or of diunsaturated fatty acids such as, in particular, (9Z,12Z)-octadeca-9,12-dienoic acid, 9-cis-octadecenoic acid or 12-hydroxy-9-cis-octadecenoic acid or of triunsaturated fatty acids such as, in particular, (6Z,9Z,12Z)-octadeca-6,9,12-trienoic acid, (9Z,12Z,15Z)-octadeca-9,12,15-trienoic acid, (8E,10E,12Z)-octadeca-8,10,12-trienoic acid, (9Z,11E,13Z)-octadeca-9,11,13-trienoic acid, (9Z,11E,13E)-octadeca-9,11,13-trienoic acid, (9E,11E,13E)-octadeca-9,11,13-trienoic acid or polyunsaturated fatty acids such as, in particular, (5Z,8Z,11Z,14Z)-eicosa-5,8,11,14-tetraenoic acid, (5Z,8Z,11Z,14Z,17Z)-eicosa-5,8,11,14,17-pentaenoic acid, (7Z,10Z,13Z,16Z,19Z)-docosa-7,10,13,16,19-pentaenoic acid, (4Z,7Z,10Z,13Z,16Z,19Z)-docosa-4,7,10,13,16,19-hexaenoic acid.

Particular preference is given to using triglycerides of epoxidized fatty acids whose fatty acids have a carbon length of 17 to 23 carbon atoms and contain at least one epoxide group.

With very particular preference, the following epoxides are used: linseed oil epoxidates, vernonia oil epoxidates, sunflower oil epoxidates, castor oil epoxidates and soybean oil epoxidates, in particular epoxidized soybean oil (CAS No. 8013-07-8).

Thiabendazole is 2-(4-thiazolyl)-1H-benzimidazole.

Iodine-containing fungicides which may be mentioned are, for example, N—(C$_1$-C$_{12}$)-alkyl-iodotetrazoles, N—(C$_6$-C$_{15}$)-aryl-iodotetrazoles, N—(C$_6$-C$_{15}$)-arylalkyl-iodotetrazoles, diiodomethyl-p-tolylsulfone, diiodomethyl-p-chlorophenylsulfone, 3-bromo-2,3-diiodo-2-propenyl alcohol, 2,3,3-tri-iodoallyl alcohol, 4-chloro-2-(2-chloro-2-methylpropyl)-5-[(6-iodo-3-pyridinyl)methoxy]-3(2H)-pyridazinone (CAS-RN: 120955-77-3), iodfenfos, 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxycarbonyl-alanine ethyl ester, 3-(3-iodopropargyl)-benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyldicarbamate, diiodomethyl-p-tolylsulfone, 3-iodo-2-propynyloxyethanol ethylcarbamate, 3-iodo-2-propynyl-oxyethanol phenylcarbamate, 3-iodo-2-propynyl thioxo thioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

Preferred iodine-containing fungicides are 3-iodo-2-propynyl 2,4,5-trichlorophenyl ether, 3-iodo-2-propynyl 4-chlorophenyl formal (IPCF), N-iodopropargyloxycarbonyl-alanine, N-iodopropargyloxycarbonyl-alanine ethyl ester, 3-(3-iodopropargyl)-benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyldicarbamate, diiodomethyl-p-tolylsulfone, 3-iodo-2-propynyloxyethanol ethylcarbamate, 3-iodo-2-propynyl-oxyethanol phenylcarbamate, 3-iodo-2-propynyl thioxo thioethylcarbamate, 3-iodo-2-propynyl carbamate (IPC), 3-bromo-2,3-diiodo-2-propenyl ethyl carbamate, 3-iodo-2-propynyl n-hexylcarbamate and 3-iodo-2-propynyl cyclohexylcarbamate.

Particularly preferred iodine-containing fungicides are 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di-(3-iodo-2-propynyl) hexyldicarbamate, 3-iodo-2-propynyloxyethanol ethylcarbamate, 3-iodo-2-propynyl-oxyethanol phenylcarbamate, 3-iodo-2-propynyl thioxo thioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate, with 3-iodo-2-propynyl butylcarbamate (IPBC) and diiodomethyl-p-tolylsulfone being even more preferred.

In addition to thiabendazole and the iodine-containing fungicide, the compositions may optionally also comprise one or more further fungicidally active compounds. This may improve mold-resistance of the PVC even more. Frequently, additional synergistic effects are also observed.

In general, all fungicides acting against mold fungi may be employed for this purpose. Here, too, it is possible to employ compositions to improve the activity even more.

The fungicides are preferably
triazoles such as:

azaconazole, azocyclotin, bitertanol, bromuconazole, cyproconazole, diclobutrazole, difenoconazole, diniconazole, epoxiconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeoconazole, (+)-cis-1-(4-chlorophenyl)-2-(1H-1,2,4-triazol-1-ypcycloheptanol, 2-(1-tert-butyl)-1-(2-chlorophenyl)-3-(1,2,4-triazol-1-yl)propan-2-ol, tebuconazole, tetraconazole, triadimefon, triadimenol, triapenthenol, tri-flumizole, triticonazole, uniconazole and their metal salts and acid adducts;

imidazoles such as:

clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chloro-phenoxy)-3,3-dimethylbutan-2-one, and their metal salts and acid adducts;

pyridines and pyrimidines such as:

ancymidol, buthiobate, fenarimol, mepanipyrin, nuarimol, pyroxyfur, triamirol;

succinate dehydrogenase inhibitors such as:

benodanil, carboxim, carboxim sulfoxide, cyclafluramid, fenfuram, flutanil, furcarbanil, furmecyclox, mebenil, mepronil, methfuroxam, metsulfovax, nicobifen, pyracarbolid, oxycarboxin, Shirlan, Seedvax;

naphthalene derivatives such as:

terbinafine, naftifine, butenafine, 3-chloro-7-(2-aza-2,7,7-trimethyloct-3-en-5-yne);

sulfenamides such as:

dichlofluanid, tolylfluanid, folpet, fluorofolpet, captan, captofol;

benzimidazoles such as:

carbendazim, benomyl, fuberidazole or their salts;

morpholine derivatives such as:

aidimorph, dimethomorph, dodemorph, falimorph, fenpropidin, fenpropimorph, tridemorph, trimorphamid and their arylsulfonate salts such as, for example, p-toluenesulfonic acid and p-dodecylphenylsulfonic acid;

benzothiazoles such as:
2-mercaptobenzothiazole;

benzothiophene dioxides such as:
N-cyclohexyl-benzo[b]thiophenecarboxamide S,S-dioxide;

benzamides such as:
2,6-dichloro-N-(4-trifluoromethylbenzyl)benzamide, tecloftalam;

boron compounds such as:
boric acid, boric esters, borax;

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethyleneisothiazolinone, 4,5-benzisothiazolinone;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzyldimethyl-dodecylammonium chloride, dichlorobenzyldimethylalkylammonium chloride, didecyldimethyl-ammonium chloride, dioctyldimethylammonium chloride, N-hexadecyltrimethylammonium chloride, 1-hexadecylpyridinium chloride, iminoctadine tris(albesilate);

iodine derivatives such as:
diiodomethyl-p-tolylsulfone, 3-iodo-2-propynyl alcohol, 4-chlorophenyl 3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;

phenols such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxy-benzoate, ethyl p-hydroxybenzoate, propyl p-hydroxybenzoate, butyl p-hydroxybenzoate, octyl p-hydroxybenzoate, 4-(2-tert-butyl-4-methylphenoxy)phenol, 4-(2-isopropyl-4-methylphenoxy)phenol, 4-(2,4-dimethylphenoxy)phenol and their alkali metal salts and alkaline earth metal salts;

pyridines such as:
1-hydroxy-2-pyridinethione (and their Cu, Na, Fe, Mn, Zn salts), tetrachloro-4-methylsulfonylpyridine, pyrimethanol, mepanipyrim, dipyrithione, 1-hydroxy-4-methyl-6-(2,4,4-trimethylpentyl)-2(1H)-pyridine;

methoxyacrylates or similar compounds such as:
azoxystrobin, dimoxystrobin, fluoxastrobin, kresoximmethyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]amino]oxy]methyl]phenyl]-3H-1,2,4-triazol-3-one (CAS No. 185336-79-2);

oxides such as:
oxides of the metals tin, copper and zinc, such as, for example, tributyltin oxide, $Cu_2O$, CuO, ZnO;

dithiocarbamates such as:
cufraneb, ferban, potassium N-hydroxymethyl-N'-methyldithiocarbamate, sodium dimethyl-dithiocarbamate, potassium dimethyldithiocarbamate, mancozeb, maneb, metam, metiram, thiram, zineb, ziram;

nitriles such as:
2,4,5,6-tetrachloroisophthalonitrile, disodium cyanodithioimidocarbamate;

quinolines such as:
8-hydroxyquinoline and the copper salts thereof;

Ag-, Zn- or Cu-containing zeolites on their own or encapsulated in polymeric materials.

Very particularly preferably, the fungicides are azaconazole, bromuconazole, cyproconazole, dichlobutrazole, diniconazole, difenconazole, hexaconazole, metaconazole, penconazole, propiconazole, tebuconazole, azoxystrobin, fludioxonil, dichlofluanid, tolylfluanid, fluorfolpet, methfuroxam, carboxin, fenpiclonil, butenafin, imazalil, N-octylisothiazolin-3-one, dichloro-N-octylisothiazolinone, mercaptobenzothiazole, thiocyanatornethyl-thiobenzothiazole, N-butyl-benzisothiazolinone, 1-hydroxy-2-pyridinethione (and their Cu, Na, Fe, Mn, Zn salts), tetrachloro-4-methylsulfonylpyridine, 3-iodo-2-propynyl n-butylcarbamate, diiodomethyl-p-tolylsulfone, bethoxazin, 2,4,5,6-tetrachloroisophthalodinitrile and carbendazirn.

Algicides to prevent the growth of algae on the PVC surfaces, or compositions which, by virtue of their unpleasant or bitter taste, prevent, for example, martens biting into flexible car parts/seals/isolations may also be optionally added.

The epoxides of the unsaturated fatty acids, fatty acid esters and fatty acid glycerides which can be used may simultaneously also be used as plasticizers. The epoxidized fatty acid esters or epoxidized fatty acid glycerides can be prepared by processes known to the person skilled in the art, for example by esterification of the epoxidized fatty acids with mono-, di- or trihydric alcohols such as, in particular, glycerol.

Particularly preferred as epoxides are epoxidized fatty acid glycerides, epoxidized fatty acid esters or epoxidized fatty acids whose fatty acids have a carbon length of 17 to 23 carbon atoms and contain at least one epoxide group. These epoxides then also preferably serve as plasticizers.

With very particular preference, the epoxides are linseed oil epoxidates, vernonia oil epoxidates, sunflower oil epoxidates and soybean oil epoxidates.

The epoxides and the iodine-containing fungicides are employed in a ratio of from 10:1 to 1:10; with preference, the epoxides are employed in a ratio of from 5:1 to 1:5; with particular preference, the epoxides and the iodine-containing fungicides are employed in a ratio of from 2:1 to 1:2. The plasticizers used are preferably phthalates, such as, in particular, diethylhexyl phthalate (DEHP), dibutyl phthalate (BBP), diisononyl phthalate (DINP), diisodecyl phthalate (DIDP), diisooctyl phthalate (DNOP), diisobutyl phthalate (DIBP), diisohexyl phthalate, diisoheptyl phthalate, di-n-octyl phthalate, diisoundecyl phthalate, diisotredecyl phthalate; adipates such as, in particular, diethylhexyl adipate (DEHA), diisooctyl adipate, diisononyl adipate, polyesters of adipinic acid or glutaric acid such as, in particular, Ultramoll® IV from Lanxess Deutschland GmbH; trialkyl esters of citric acid or acetylated trialkyl esters of citric acid such as, in particular, acetyl tributyl citrate (ATBC); esters of trimellitic acid such as, in particular, tri(2-ethylhexyl) trimellitate, tri(isooctyl) trimellitate, tri(isononyl) trimellitate; 1,2-dicyclohexyl-based plasticizers such as, in particular, 1,2-cyclo-hexanedicarboxylic acid dinonyl ester (Hexamoll®, DING); alkylsulfonic esters of phenol such as, in particular, Mesamoll® from Lanxess Deutschland GmbH (CAS-No. 091082-17-6); acetylated mono- and diglycerides; benzoic acid diesters, in particular of dialkylene glycols, such as, in particular, dipropylene glycol dibenzoate, or isononyl benzoate; trimethylolpropane esters such as, in particular, trimethylolpropane benzoate 2-ethylhexanoate mixtures; dialkyl esters of terephthalic acid such as, in particular, di-2-ethylhexyl terephthalate.

However, it is preferred not to add any further plasticizers but to employ epoxidized fatty acid glycerides, epoxidized fatty acid esters or epoxidized fatty acids which, as epoxides, stabilize the composition of TBZ and IPBC and additionally assume the function of the plasticizer.

Here, the plasticizers can either be employed as a single component, or else also consist of compositions of a plurality of plasticizers.

In addition, further auxiliaries such as, for example, thixotropic agents and stabilizers may be added to the mixture. Thixotropic agents are generally all substances capable of stabilizing dispersions of thiabendazole and optionally other fungicides in plasticizers and thus preventing sedimentation of the active compounds.

The thixotropic agents are preferably inorganic thixotropic agents such as modified sheet silicates, fumed silica or precipitated silica or organic thixotropic agent such as castor oil derivatives or mono-, di- or triglycerides of castor oil derivatives, in particular mono-, di- or triglycerides of (12R)-cis-12-hydroxyoctadec-9-enoic acid, (9Z,12R)-12-hydroxyoctadec-9-enoic acid or 12-hydroxyoctadecanoic acid, esters or amides of ricinoleic acid or their salts, modified polyamides or fatty acid amides, modified polyamide waxes such as, in particular, Luvotix® HP from Lehmann & Voss, Hamburg, Germany, polyolefins with thixotropic action such as, in particular, Luvotix® P25x from Lehmann 8z Voss, Hamburg, Germany, urea derivatives or specifically modified alkyd resins or compositions thereof.

The thixotropic agents are particularly preferably castor oil derivatives such as, for example, hydrogenated castor oil, sulfated castor oil (CAS 8002-33-3), castor oil derivatized with polyamides or fatty acid amides, in particular Luvotix® HT from Lehmann & Voss, Hamburg, Germany, inorganically modified castor oil, silicate-modified castor oil such as, in particular, Luvotix® ZR 50 from Lehmann & Voss, Hamburg, Germany, modified polyamides such as Rilanit® plus from Cognis, modified polyamide axes such as, in particular, Luvotix® w HP from Lehmann & Voss, Hamburg, Germany, polyolefins with thixotropic action such as, in particular, Luvotix® P25x or Luvotix® P50 from Lehmann & Voss, Hamburg, Germany, alkyd resins with thixotropic action having, for example, urea structures or being urethanized, or triglycerides of ricinoleic acid derivatives, in particular triglycerides of (12R)-cis-12-hydroxyoctadec-9-enoic acid, (9Z,12R)-12-hydroxyoctadec-9-enoic acid or 12-hy-droxyoctadecanoic acid, esters or amides of ricinoleic acid or their salts. The triglycerides of ricinoleic acid derivatives, of ricinoleic acid or of hydrogenated ricinoleic acid (12-hydroxyoctadecanoic acid), their esters or their amides and salts thereof can be employed in compositions for protecting thermoplastic polymers which may optionally comprise further saturated, unsaturated, branched or straight-chain fatty acids. Preference is given to using the triglycerides of ricinoleic acid derivatives, of ricinoleic acid or of hydrogenated ricinoleic acid (12-hydroxyoctadecanoic acid), their esters or their amides and salts thereof in the compositions for protecting thermoplastic polymers.

With very particular preference, the castor oil derivative employed is hydrogenated castor oil (CAS No. 8001-78-3) as contained, for example, in Luvotix® R from Lehmann & Voss, Hamburg, Germany.

It is also possible to use other thixotropic agents or compositions of thixotropic agents. The thixotropic agents that may be employed are generally commercially available and are usually also employed in solvent-based paints to prevent settling of the pigments. To improve properties such as temperature sensitivity, UV stability, oxidation stability of the dispersions themselves, the dispersions during incorporation into the PVC and the PVC preparations prepared therefrom even more, it is possible to employ stabilizers.

The stabilizers which can optionally be employed may be antioxidants, free radical scavengers or UV absorbers. One or more of these substances may optionally be employed.

Examples of stabilizers which may be mentioned are:
sterically hindered phenols, such as
2,6-di-tert-butyl-4-methylphenol, 2-tert-butyl-4,6-dimethylphenol, 2,6-di-cyclopentyl-4-methylphenol, 2-(α-methylcyclohexyl)-4,6-dimethylphenol, 2,6-di-octadecyl-4-methylphenol or 2,6-di-tert-butyl-4-methoxymethylphenol, diethyl (3,5-di-tert-butyl-4-hydroxybenzyl)phosphonate, 2,4-dimethyl-6-(1-methylpentadecyl)phenol, 2-methyl-4,6-bis[(octylthio)methyl]phenol, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,2'-thiobis (6-tert-butyl-4-methy)phenol), 2,2'-thio-bis(4-octylphenol), 4,4'-thiobis(6-tert-butyl-3-methylphenol), 4,4"-thiobis(6-tert-butyl-2-methyl-phenol), 2,2'-methylenebis(6-tert-butyl- 4-methylphenol), 2,2'-methylenebis(4-methyl-6-cyclohexyl-phenol), 2,2'-methylenebis(4,6-di-tert-butylphenol), 2,2'-ethylidenebis(4,6-di-tert-butylphenol), 4,4'-methylenebis(2,6-di-tert-butylphenol), 4,4'-methylenebis(6-tert-butyl-2-methylphenol), 1,1-bis(5-tort-butyl-4-hydroxy-2-methylphenyl)butane, 1,1,3-tris(5-tert-butyl-4-hydroxy-2-methyl-phenyl)butane, 1,3,5-tri(3,5-di-tert-butyl-4-hydroxybenzyl)-2,4,6-trimethylbenzene, isooctyl 3,5-di-tert-butyl-4-hydroxybenzylmercaptoacetate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 1,3,5-tris[(3,5-di-tert-butyl-4-hydroxyphenyl) propionyloxyethyl] isocyanurate, dioctadecyl 3,5-di-tert-butyl-4-hydroxy-benzylphosphonate, calcium monoethyl 3,5-di-tert-butyl-4-hydroxybenzylphosphonate, N,N'-di-(3,5-di-tert-butyl-4-hydroxyphenylpropionyl)hexamethylenediamine, N,N-di-(3,5-di-tert-butyl-4-hydroxyphenylpropionyl)trimethylenediamine, N,N'-di-(3,5-di-tert-butyl-4-hydroxyphenylpropionyphydrazine, 3,9-bis[1,1-dimethyl-2-[(3-tert-butyl-4-hydroxy-5-methylphenyl)propionyloxy] ethyl]-2,4,8,10- tetraoxaspiro[5.5]undecane, bis[3,3-bis(4'-hydroxy-3'-tert-butylphenyl)butanoic acid]ethylene glycol ester, 2,6-bis[[3-(1,1-dirnethylethyl)-2-hydroxy-5-methylphenyl]octahydro-4,7-methano-1H-indenyl]-4-methylphenol (=Wingstay L), 2,4-bis(n-octylthio)-6-(3,5-di-tert-butyl-4-hydroxyphenylamino)-s-triazine, N-(4-hydroxy-phenyl) octadecaneamide, 2,4-di-tert-butylphenyl 3',5'-di-tert-butyl-4'-hydroxybenzoate, (benzoic acid, 3,5-bis(1,1-dimethylethyl)-4-hydroxy-, hexadecyl ester), 3-hydroxyphenyl benzoate, 2,2'-methylenebis(6-tert-butyl-4-methylphenol) monoacrylate, 2-(1,1-dimethylethyl)-6-[1-[3-(1,1-dimethylethyl)-5-(1,1-dimethylpropyl)-2-hydroxyphenyl]ethyl]-4-(1,1-dimethylpropyl)phenyl ester, esters of β-(3,5-di-tert-butyl-4-hydroxyphenyl)propionic acid with monohydric or polyhydric alcohols such as, in particular, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide, esters of β-(5-tert-butyl-4-hydroxy-3-methylphenyl)propionic acid with monohydric or polyhydric alcohols such as, in particular, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide.

Hindered amines, such as bis(1,2,2,6,6-pentamethyl-4-piperidyl) 2-(3,5-di-tert-butyl-4-hydroxybenzyl)-2-butylmalonate, bis(2,2,6,6-tetramethyl-4-piperidyl)decanedioate, dimethyl succinate-1-(2-hydroxyethyl)-4-hydroxy-2,2,6,6-tetramethylpiperidine copolymer, poly[[6-[(1,1,3,3-tetramethylbutyl)amino]-1,3,5-triazine-2,4-diyl][(2,2,6,6-tetramethyl-4-piperidyl)iminolene[(2,2,6,6-tetramethyl-4-piperidyl)imino]] (CAS No. 71878-19-8), 1,5,8,12-tetrakis[4,6-bis(n-butyl-n-1,2,2,6,6-pentamethyl-4-piperidylamino)-1,3,5-triazin-2-yl]-1,5,8,12-tetraazadodecane (CAS No. 106990-43-6), bis(1,2,2,6,6-pentamethyl-4-piperidyl)decanedioate, bis(1,2,2,6,6-pentamethyl-4-piperidyl) 2-(3,5-di-tert-butyl-4-hydroxybenzyl)-2-butylmalonate, decanedioic acid, bis(2,2,6,6-tetramethyl-4-piperidinyl) ester, reaction products with tert-butyl hydroperoxide and octane (CAS No. 129757-67-1), Chimasorb 2020 (CAS No. 192268-64-7), poly[[6-morpholino-1,3,5-triazine-2,4-diyl][(2,2,6,6-tetramethyl-4-piperidinypimino)-1,6-hexane-diyl[(2,2,6,6-tetramethyl-4-piperidinyeiminon poly[[6-(4-morpholinyl)-1,3,5-triazine-2,4-diyl]-[(1,2,2,6,6-pentamethyl-4-piperidinypimino]-1,6-hexanediyl[(1,2,2,6,6-pentamethyl-4-piperidinyl)-imino]] (9CI), 3-dodecyl-1-(2,2,6,6-tetramethyl-4-piperidyl) pyrrolidine-2,5-dione, 3-dodecyl-1-(1,2,2,6,6-pentamethylpiperidin-4-yl)pyrrolidine-2,5-dione, 4-octadecanoyloxy-2,2,6,6-tetramethyl-piperidine, poly[[6-(cyclohexylamino)-1,3,5-triazine-2,4-diyl][(2,2,6,6-tetramethyl-4-piperidinyl)-imino]-1,6-hexanediyl[(2,2,6,6-tetramethyl-4-piperidinypimino]], 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-(CAS No. 109423-00-9), N,N'-bis(formyl)-N,N'-bis(2,2,6,6-tetramethyl-4-piperidyl)-1,6-hexane-diamine, N-(tetramethyl-4-piperidinyemaleimide-C20-24-α-olefin copolymer (CAS No. 199237-39-3), tetrakis(1,2,2,6,6-pentamethyl-4-piperidyl) 1,2,3,4-butanetetracarboxylate, tetrakis(2,2,6,6-tetramethyl-4-piperidyl) 1,2,3,4-butanetetracarboxylate, 1,2,2,6,6-pentamethyl-4-piperidinyl tridecyl 1,2,3,4-butanetetracarboxylate, (1,2,3,4-butanetetracarboxylic acid, 2,2,6,6-tetramethyl-4-piperidinyl tridecyl ester), (2,4,8,10-tetraoxaspiro[5.5]undecane-3,9-diethanol, β,β,β',β'-tetramethyl-, polymer with 1,2,3,4-butanetetracarboxylic acid) (CAS No. 115055-30-6), 2,2,4,4-tetramethyl-21-oxo-7-oxa-3,20-diazadispiro[5.1.11.2] heneicosane, (7-oxa-3,20-diazadispiro[5.1.11.2]heneicosane-20-propanoic acid, 2,2,4,4-tetramethyl-21-oxo-, tetradecyl ester), (7-oxa-3,20-diazadispiro[5.1.11.2]heneicosan-21-one, 2,2,4,4-tetramethyl-20-(oxiranylmethyl)-), (propanamide, N-(2,2,6,6-tetramethyl-4-piperidinyl)-3-[(2,2,6,6-tetramethyl-4-piperidinyl)amino]-), (1,3-propanediamine, N,N"-1,2-ethanediylbis-, polymer with 2,4,6-trichloro-1,3,5-triazine, reaction products with N-butyl-2,2,6,6-tetramethyl-4-piperidin-amine) (CAS No. 136504-96-6), 1,1'-ethylenebis(3,3,5,5-tetramethyl-2-piperazinone), (piperazinone, 1,1',1"-[1,3,5-triazine-2,4,6-triyltris[(cyclohexylimino)-2,1-ethanediyl]] tris[3,3,5,5-tetramethyl-), (7-oxa-3,20-diazadispiro [5.1.11.2]heneicosane-20-propanoic acid, 2,2,4,4-tetramethyl-21-oxo-, dodecyl ester), 1,1-bis(1,2,2,6,6-pentamethyl-4-piperidyloxycarbonyl)-2-(4-methoxyphenypethene, (2-propenoic acid, 2-methyl-, methyl ester, polymer with 2,2,6,6-tetramethyl-4-piperidinyl 2-propenoate) (CAS No. 154636-12-1), (propanamide, 2-methyl-N-(2,2,6,6-tetrarnethyl-4-piperidinyl)-2-[(2,2,6,6-tetramethyl-4-piperidinyl)amino]-), (D-glucitol, 1,3:2,4-bis-O-(2,2,6,6-tetramethyl-4-piperidinylidene)-) (CAS No. 99473-08-2), N,N'-bis(2,2,6,6-tetramethyl-4-piperidinypisophthalamide, 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, 1-(4-tert-butyl-2-butenyl)-4-hydroxy-2,2,6,6-tetramethy-lpiperidine, 4-stearoyloxy-2,2,6,6-tetramethylpiperidine, 1-ethyl-4-salicyloyloxy-2,2,6,6-tetramethyl-piperidine, 4-methacryloyloxy-1,2,2,6,6-pentamethylpiperidine, 1,2,2,6,6-pentamethylpiperidin-4-yl β-(3,5-di-tert-butyl-4-hydroxyphenyl) propionate, 1-benzyl-2,2,6,6-tetramethyl-4-piperidinyl maleate, (di-2,2,6,6-tetramethylpiperidin-4-yl) adipate, (di-2,2,6,6-tetramethylpiperidin-4-yl) sebacate, (di-1,2,3,3,6-tetramethyl-2,6-diethylpiperidin-4-yl) sebacate, (di-1-allyl-2,2,6,6-tetramethyl-piperidin-4-yl) phthalate, 1-propargyl-4-β-cyanoethyloxy-2,2,6,6-tetramethylpiperidine, 1-acetyl-2,2,6,6-tetramethylpiperidin-4-yl acetate, trimellitic acid tri(2,2,6,6-tetramethylpiperidin-4-yl) ester, 1-acryloyl-4-benzyloxy-2,2,6,6-tetramethylpiperidine, dibutyl-malonic acid di(1,2,2,6,6-pentamethyl-piperidin-4-yl) ester, butyl(3,5-di-tert-butyl-4-hydroxybenzyl)malonic acid di(1,2,2,6,6-pentamethyl-piperidin-4-yl) ester, dibenzylmalonic acid di(1,2,2,6,6-pentamethylpiperidin-4-yl) ester, dibenzylmalonic acid di(1,2,3,6-tetramethyl-2,6-diethylpiperidin-4-yl) ester, hexane-1',6'-bis-(4-carbamoyloxy-1-n-butyl-2,2,6,6- tetramethylpiperidine), toluene-2',4'-bis(4-carbamoyloxy-1-n-propyl-2,2,6,6-tetramethylpiperidine), dimethyl-bis(2,2,6,6-tetramethylpiperidine-4-oxy)silane, phenyl-tris(2,2,6,6-tetramethylpiperidine-4-oxy)silane, tris(1-propyl-2,2,6,6-tetramethylpiperidin-4-yl) phosphite, tris(1-propyl-2,2,6,6-tetramethylpiperidin-4-yl) phosphate, phenyl[bis(1,2,2,6,6-penta-methylpiperidin-4-yl)phosphonate, di(1,2,2,6,6-pentamethylpiperidin-4-yl) sebacate, N,N'-bis(2,2,6,6-tetramethylpiperidin-4-yl)hexamethylene-1,6-diamine, N,N'-bis(2,2,6,6-tetramethylpiperidin-4-yl)-hexamethylene-1,6-diacetamide, 1-acetyl-4-(N-cyclohexylacetamido)-2,2,6,6-tetramethylpiperidine, 4-benzylamino-2,2,6,6-tetramethylpiperidine, N,N'-bis(2,2,6,6-tetramethylpiperidin-4-yl)-N,N'-dibutyladipamide, N,N-bis(2,2,6,6-tetramethylpiperidin-4-yl)-N,N'-dicyclohexyl(2-hydroxypropylene), N,N'-bis(2,2,6,6-tetramethylpiperidin-4-yl)-p-xylylenediamine, 4-(bis-2-hydroxy-ethyl)amino-1,2,2,6,6-pentamethylpiperidine, 4-(3-methyl-4-hydroxy-5-tert-butyl-benzamido)-2,2,6,6-tetramethylpiperidine, 4-methacrylamino-1,2,2,6,6-pentamethylpiperidine, 9-aza-8,8,10,10-tetramethyl-1,5-dioxaspiro[5.5]undecane, 9-aza-8,8,10,10-tetramethyl-3-ethyl-1,5-dioxaspiro[5.5]undecane, 8-aza-2,7,7,8,9,9-hexamethyl-1,4-dioxaspiro[4.5]decane, 9-aza-3-hydroxymethyl-3-ethyl-8,8,9,10,10-pentamethyl-1-5-dioxaspiro[5.5]undecane, 9-aza-3-ethyl-3-acetoxymethyl-9-acetyl-8,8,10,10-tetramethyl-1,5-dioxaspiro[5.5]undecane, 2,2,6,6-tetramethylpiperidine-4-spiro-2'-(1',3'-dioxane)-5'-spiro-5"-(1",3"-dioxane)-2"-spiro-4"-(2"',2"',6"',6"'- tetramethylpiperidine), 3-benzyl-1,3,8-triaza-7,7,9,9-tetramethyl-spiro[4.5]decane-2,4-dione, 3-n-octyl-1,3,8-triaza-7,7,9,9-tetramethyl-spiro[4.5]decane-2,4-dione, 3-allyl-1,3,8-triaza-1,7,7,9,9-penta-methyl-spiro[4.5]decane-2,4-dione, 3-glycidyl-1,3,8-triaza-7,7,8,9,9-pentamethyl-spiro[4.5]-decane-2,4-dione, 2-isopropyl-7,7,9,9-tetramethyl-1-oxa-3,8-diaza-4-oxyspiro[4.5]decane, 2-butyl-7,7,9,9-tetramethyl-1-oxa-3,8-diaza-4-oxyspiro[4.5]decane, 2-isopropyl-7,7,9,9-tetramethyl-1-oxa-4,8-diaza-oxyspiro[4.5]decane, 2-butyl-7,7,9,9-tetramethyl-1-oxa-4,8-diaza-3-oxyspiro[4.5]decane, bis[β-(2,2,6,6-tetramethylpiperidino)ethyl] sebacate, α-(2,2,6,6-tetramethylpiperidino)acetic acid n-octyl ester, 1,4-bis(2,2,6,6-tetramethylpiperidino)-2-butene, N-hydroxymethyl-N'-2,2,6,6-tetra-methylpiperidin-4-ylurea, N-methoxymethyl-N'-2,2,6,6-tetramethylpiperidin-4-ylurea, N-methoxymethyl-N'-n-dodecyl-N'-2,2,6,6-tetramethylpiperidin-4-ylurea, O-(2,2,6,6-tetramethyl-piperidin-4-yl)-N-methoxymethylurethane.

Phosphites and phosphonates, such as tris(nonylphenyl) phosphite, tris(2,4-di-tert-butylphenyl) phosphite, bis(2,4-di-tert-butylphenyl) pentaerythritol diphosphite, bis(2,6-di-tert-butyl-4-methylphenyl)pentaerythritol diphosphite, 2,2'-methylenebis(4,6-di-tert-butylphenyl) octyl phosphite, tetrakis(2,4-di-tert-butylphenyl)-[1,1'-biphenyl]-4,4'-diylbisphosphonite, 2,2'-ethylidenebis(4,6-di-tert-butylphenyl) fluorophosphite, dioctadecyl pentaerythritol diphosphonite, 2-[[2,4,8,10-tetrakis(1,1-dimethylethyl)dibenzo[d,f][1,3,2]-dioxaphosphin-6-yl]oxy]-N,N-bis[2-[2,4,8,10-tetrakis(1,1-dimethylethyl)dibenzo[d,f][1,3,2]-dioxaphosphin-6-yl]oxy]ethyl]ethanamine (CAS No. 80410-33-9), bis(2,4-di-tert-butyl-6-methyl-phenyl) ethyl phosphite, 2,4,6-tri-tert-butylphenyl 2-butyl-2-ethyl-1,3-propanediol phosphite, bis(2,4-dicumylphenyl) pentaerythritol diphosphite, hydroxylamines, such as amines, bis(hydrogenated tallow alkyl), oxidized,
secondary arylatnines, such as:

N-(2-naphthyl)-N-phenylamine, 2,2,4-trimethyl-1,2-dihydroquinoline polymer (CAS No. 26780-96-1), N-2-propyl-N'-phenyl-p-phenylenediamine, N-(1-naphthyl)-N-phenylamine, (benzenamine, N-phenyl-, reaction products with 2,4,4-trimethylpentene) (CAS No. 68411-46-1), 4-(1-methyl-1-phenylethyl)-N-[4-(1-methyl-1-phenylethyl)phenyl]aniline.

Lactones and benzofuranones, such as

Irganox HP 136 (CAS No. 181314-48-7)

Thioethers and thioesters, such as distearyl 3,3-thiodipropionate, dilauryl 3,3'-thiodipropionate, ditetradecyl thiodipropionate, di-n-octadecyl disulfide.

UV absorbers, such as (methanone, [methylenebis(hydroxymethoxyphenylene]bis[phenyl-), (methanone, [1,6-hexanediylbis-[oxy(2-hydroxy-4,1-phenylene)]]bis[phenyl-), 2-benzoyl-5-methoxyphenol, 2,4-dihydroxybenzo-phenone, 2,2'-dihydroxy-4-methoxybenzophenone, 2-hydroxy-4-octyloxybenzophenone, 2-hydroxy-4-dodecyloxybenzophenone, 2-(2-hydroxy-4-hexyloxyphenyl)-4,6-diphenyl-1,3,5-triazine, 2,4-bis(2,4-dimethylphenyl)-6-(2-hydroxy-4-octyloxyphenyl)-1,3,5-triazine, 2-ethoxy-2'-ethyloxalic acid bisanilide, N-(5-tert-butyl-2-ethoxyphenyl)-N'-(2-ethylphenyl)oxamide, dimethyl (p-methoxy-benzylidene)malonate, 2,2"-(1,4-phenylene)bis[3,1-benzoxazin-4-one], N'-(4-ethoxycarbonyl-phenyl)-N-methyl-N-phenylformamidine, 4-methoxycinnarnic acid 2-ethylhexyl ester, 4-methoxycinnamic acid isoamyl ester, 2-phenylbenzimidazole-5-sulfonic acid, 2-cyano-3,3-diphenylacrylic acid 2-ethylhexyl ester, 2-ethylhexyl salicylate, 3-(4-methylbenzylidene)bornan-2-one.

By using the compositions according to the invention, the PVC is protected against attack by mold fungi.

Mold fungi of the following genera may be mentioned as examples:

*Alternaria* such as *Alternaria tenuis,*
*Aspergillus* such as *Aspergillus niger,*
*Chaetomium* such as *Chaetomium globosurn,*
*Coniophora* such as *Coniophora puetana,*
*Lentinus* such as *Lentinus tigrinus,*
*Penicillium* such as *Penicillium glaucum,*
*Polyporus* such as *Polyporus versicolor,*
*Aureobasidium* such as *Aureobasidium pullulans,*
*Sclerophoma* such as *Sclerophoma pityophila,*
*Trichoderma* such as *Trichoderma viridae*

The compositions according to the invention are suitable for equipping thermoplastic plastics.

The material to be equipped is preferably a polymeric halogen-containing vinyl compound such as, for example, polyvinyl chloride (PVC) and polyvinylidene chloride or a copolymer of vinyl chloride/vinylidene chloride, vinyl chloride/vinyl acetate, vinylidene chloride/vinyl acetate.

The compositions of the polymeric halogen-containing vinyl compounds may also comprise further plastics which act by way of example as polymeric processing aids or impact modifiers. These further plastics are selected from the group consisting of the homo- and copolymers based on ethylene, propylene, butadiene, vinyl acetate, glycidyl acrylate, glycidyl methacrylate, acrylates and methacrylates with alcohol components of branched or unbranched $C_1$-$C_{10}$ alcohols, styrene or acrylonitrile. Particular preference is given to polyacrylates having identical or different alcohol moieties from the group of the $C_4$-$C_8$ alcohols, in particular of butanol, hexanol, octanol and 2-ethylhexanol, polymethyl methacrylate, methyl methacrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers and methyl methacrylate-styrene-butadiene copolymers.

However, the compositions according to the invention are also suitable for equipping other thermoplastic plastics such as, for example, polyethene (PE), polypropene (PP), polystyrene (PS), polyacrylonitrile (PAN), polyamides (PA), polyesters (PES), polyacrylates or compositions of these.

The compositions according to the invention can be incorporated into the PVC using known methods, for example by extrusion or calendering. Here, the compositions are either mixed with the auxiliaries (thixotropic agents, plasticizers, stabilizers, dyes and pigments, fillers, etc.) for PVC production and then incorporated. However, it is also possible to incorporate the compositions into the finished PVC. The appropriate methods are known in the art and are widely employed in industrial production.

The invention also embraces a process for preparing polymeric products from thermoplastic polymers, in particular from polyvinyl chloride, at least one epoxide, thiabendazole and at least one iodine-containing fungicide, where the composition according to the invention of at least one epoxide, thiabendazole and at least one iodine-containing fungicide is incorporated into the thermoplastic polymer, in particular into polyvinyl chloride, by extrusion, calendering or compounding.

The invention also embraces a process for preparing the compositions according to the invention where at least one epoxide, thiabendazole and at least one iodine-containing fungicide are mixed. The mixing process can take place by stirring or grinding, and by all customary compounding processes known to the skilled person from the state of the art. The compositions are preferably mixed by dispersing. Particularly preferably, the compositions are mixed by dispersing and, in a further step, ground using dispersing apparatuses. Appropriate processes and apparatuses such as bead mills or stator/rotor dispersing apparatuses are known to the skilled person from the state of the art.

In general, the composition according to the invention comprising thiabendazole, at least one epoxide and at least one iodine-containing fungicide is employed in an amount of from 0.1 to 10% by weight, preferably 0.2 to 5.0% by weight, based on the polymer to be protected.

In general, the composition according to the invention comprising thiabendazole, at least one epoxide and at least one iodine-containing fungicide is employed in an amount of from 0.1 to 10% by weight, preferably 0.2 to 5.0% by weight, based on the polyvinyl chloride to be protected.

The invention furthermore embraces polymeric products comprising thermoplastic polymers, thiabendazole, at least one epoxide and at least one iodine-containing fungicide. In particular, the invention embraces a mixture of polyvinyl chloride, thiabendazole, at least one epoxide and at least one iodine-containing fungicide.

The mixture according to the invention or the polymeric product of at least one thermoplastic polymer, in particular polyvinyl chloride, thiabendazole, at least one epoxide and at least one iodine-containing fungicide is further processed according to the known processes. It is used for the production of pipelines, of cables, of wire sheathing, in internal fittings, or in the construction of vehicles or of furniture, in floor coverings, in medical items, in food-or-drink packing, in gaskets, in tarpaulins, in foils, including composite foils and foils for laminated safety glass, particularly for the vehicle sector and for the architecture sector, or in synthetic leather, toys, packaging containers, adhesive-tape foils, apparel, coatings, or else fibers for textiles.

The composition according to the invention is suitable in particular for preparing mixtures or polymeric products comprising polyvinyl chloride, thiabendazole, at least one epoxide and at least one iodine-containing fungicide, since the compositions according to the invention have high stability. Since decomposition of the iodine-containing fungicide is reduced, the mixtures according to the invention also have improved efficacy.

The invention also embraces the use of the compositions according to the invention for protecting polymers, in particular for protecting polyvinyl chloride, against attack or destruction by microorganisms.

Additionally, the invention, by employing the epoxides of the unsaturated fatty acids, fatty acid esters and fatty acid glycerides, allows the additional use of possibly toxic plasticizers such as phthalates to be dispensed with.

For clarification, it should be mentioned that the scope of the invention encompasses all specified, general or preferred definitions and parameters in any combinations.

EXAMPLES

Materials and Abbreviations
  Luvotix® R=hydrogenated castor oil CAS No. 8001-78-3 from Lehmann & Voss, Hamburg, Germany
  Mesamoll®=alkylsulfonic ester of phenol
  DINP=diisononyl phthalate
  ESBO=epoxidized soybean oil CAS No. 8013-07-8; Baerostab LSA, from Baerlocher, Lingen, Germany
  Vinnolit S 4170=suspensions-PVC for thermoplastic processing from Vinnolit GmbH & Co. KG, Germany
  Irgastab® CZ 11=PVC stabilizer based on calcium/zinc carboxylate
  TBZ=thiabendazole Comparative Example 1

With stirring, 140.4 g of dichloroctylisothiazolinone (DCOIT) are dissolved in 559.6 g of diisononyl phthalate (DINP). This gives 700 g of a yellow solution having a DCOIT content of 20% (HPLC)

Comparative Example 2

With stirring, 140.0 g of octylisothiazolinone (OIT) are dissolved in 560.0 g of diisononyl phthalate (DINP). This gives 700 g of a light-yellow solution having an OIT content of 20% (HPLC)

Example 3

1.40 g of Luvotix® R (Lehmann & Voss, Hamburg; hydrogenated castor oil CAS No. 8001-78-3), 28.13 g of ESBO (epoxidized soybean oil; CAS No. 8013-07-8) and 27 g of iodopropargyl butylcarbamate (IPBC) are dissolved in 559.13 g of diisononyl phthalate (DINP), 135 g of thiabendazole (TBZ) are incorporated at the dissolver and the mixture is stirred at 4000 rpm for 45 min. The liquid pre-dispersion is then ground twice on a ball mill (DYNO-Miihle Multi Lab). This gives a highly thixotropicized dispersion which is, however, processable after stirring.
  Yield: 602 g
  Viscosity: 1000 mPas (30 l/s)
  Content (HPLC): 3.5% IPBC/18.4% TBZ After 2 months of storage at 40° C., there are no signs of sedimentation.

Example 4 (Stabilization of Iodine-Containing Fungicides)

Dispersion 1

0.6 g of Luvotix® R is dissolved in 79.4 g of Mesamoll®, 120 g of TBZ, a further 400 g of Mesamoll® are added and incorporated at the dissolver. The mixture is stirred at 4000 rpm for 45 min.

The liquid pre-dispersion is then passed twice through a ball mill (DYNO-Mithle Multi Lab).

This gives 414 g of a highly thixotropic, white dispersion
Viscosity: 1533 mPas/30.1 s
Content (HPLC): 20% TBZ
Stock Dispersion (Example 4-1)

50 g of dispersion 1 are mixed with 80 g of a 2.5% strength solution of IPBC in Mesamoll®.

This gives 130 g of a dispersion
Content (HPLC): 7.69% TBZ/1.54% IPBC

To assess the stabilizing action of ESBO (epoxidized soybean oil), the amounts of ESBO mentioned below were incorporated and the resulting dispersions were stored in a comparable manner at 40° C.:

TABLE 1

(Composition of the ESBO-containing dispersions)

| Example | Amount of stock dispersion [g] | Amount of ESBO [g] |
|---|---|---|
| 4-1 | 20 | — |
| 4-2 | 20 | 0.31 |
| 4-3 | 20 | 0.155 |
| 4-4 | 20 | 0.10 |
| 4-5 | 20 | 0.62 |
| 4-6 | 20 | 1.24 |

TABLE 2

(Storage of the formulations from Table 1 at 40° C.)

|  | 4-1 | 4-2 | 4-3 | 4-4 | 4-5 | 4-6 |
|---|---|---|---|---|---|---|
| IPBC content (start) [%] | 1.4 | 1.4 | 1.4 | 1.4 | 1.4 | 1.4 |
| IPBC content (1 month 40° C.) [%] | 1.0 | 1.5 | 1.5 | 1.4 | 1.5 | 1.4 |
| IPBC content (2 months 40° C.) [%] | 0.02 | 1.5 | 1.5 | 1.5 | 1.5 | 1.4 |
| TBZ content (start) [%] | 7.6 | 7.7 | 7.7 | 7.8 | 7.6 | 7.6 |
| TBZ content (1 month 40° C.) [%] | 7.9 | 7.7 | 7.7 | 7.7 | 7.5 | 7.2 |
| TBZ content (2 months 40° C.) [%] | 7.6 | 7.5 | 7.7 | 7.5 | 7.5 | 7.3 |

After only one month of storage at 40° C., the dispersion 4-1 (without ESBO) shows strong brown discoloration, whereas the dispersions equipped with ESBO only had a weak yellowish discoloration even after 3 months of storage at 40° C.

Example 5 (Incorporation of the Dispersions into PVC)

100 parts of Vinnolit S 4170
3.0 parts of Irgastab CZ 11
4.0 parts of ESBO (epoxidized soybean oil)
54 parts of DINP (diisononyl phthalate)

X parts of the dispersion according to the invention (see Table 3)

are intensively mixed with one another in a plastic beaker and then homogenized using a calender heated to 180° C. The resulting cooled sheets were then used to prepare 200×200×2 mm test specimens.

TABLE 3

(Preparation of the PVC test specimens)

| Ex. No. | Dispersion of Ex. No. used | Parts in the PVC formulation (v.s.) | Total active compound content in ppm |
|---|---|---|---|
| 5-1 | none | 0 | 0 |
| 5-2 | 1 | 0.81 | 1000 |
| 5-3 | 1 | 0.60 | 750 |
| 5-4 | 2 | 0.81 | 1000 |
| 5-5 | 2 | 0.60 | 750 |
| 5-18 | 3 | 1.43 | 2000 |
| 5-19 | 3 | 1.07 | 1500 |
| 5-20 | 3 | 0.72 | 1000 |

Example 6 (Mold Resistance of the PVC Samples)

Following ISO 846, the samples were assessed for their biological activity.

The PVC sample from Example 26 are in each case cut into 2×2 cm pieces, one test specimen is aged in running water for 120 h, the other one is tested without any prior treatment.

The test specimens are placed on a malt agar (in Petri dishes) contaminated with a mixed spore suspension of *Penicillium funicolosum* (ATCC 36839), *Chaetomium globosum* (ATCC 6205), *Trichoderma longibrachiatum* (ATCC 9645), *Paecilomyces variotii* (ATCC 18502) and *Aspergillus niger* (ATCC 6275) and incubated at 26° C. and 80% rel. atmospheric humidity for two weeks The furnal growth on the agar plates is then examined with a stereo magnifying glass and assessed in accordance with the following scheme:

TABLE 4

(Assessment scheme)

| Assessment | Description |
|---|---|
| 0 | insufficient mold resistance sample >10% overgrown |
| 1 | moderate mold resistance sample at most 10% overgrown |
| 2 | good mold resistance sample not overgrown, or only at the edge, no zone of inhibition around the test specimen |
| 3 | very good mold resistance sample not overgrown, there is a zone of inhibition around the test specimen |

For the samples tested, the following assessments were obtained:

TABLE 5

(Biological assessment of mold resistance)

| Sample of Ex. No. | Assessment without watering | Assessment after watering (120 h) | Active compound content in ppm |
|---|---|---|---|
| 5-1 (Zero sample) | 0 | 0 | 0 |
| 5-2 (Comparison 1) | 0 | 0 | 1000 |
| 5-4 (Comparison 2) | 1-2 | 0-1 | 1000 |
| 5-20 | 3 | 3 | 1000 |

What is claimed is:

1. A fungicidal composition comprising:
   at least one epoxide selected from triglycerides of epoxidized fatty acids whose fatty acids have a carbon length of 17 to 23 carbon atoms and contain at least one epoxide group; and
   fungicide components having fungicidal activity, the fungicide components comprising:
   thiabendazole, salts of thiabendazole, and/or acid addition compounds of thiabendazole, and
   at least one iodine-containing fungicide selected from 3-iodo-2-propynyl butylcarbamate (IPBC), diiodomethyl-p-tolylsulfone, and mixtures thereof,
   wherein a ratio of epoxides to iodine-containing fungicides is 10:1 to 1:10.

2. The composition as claimed in claim 1, wherein the epoxides are selected from the group consisting of linseed oil epoxidates, vernonia oil epoxidates, sunflower oil epoxidates, castor oil epoxidates, and soybean oil epoxidates.

3. The composition as claimed in claim 1, wherein he ratio of epoxides to iodine-containing fungicides is 2:1 to 1:2.

4. The composition according to claim 1, further comprising at least one of algaecides and further fungicidally active compounds.

5. The composition according to claim 4, wherein the at least one further fungicidally active compound is selected from the group consisting of triazoles, imidazoles, pyridines, pyrimidines, naphthalene derivatives, sulfenamides, benzimidazoles, morpholine derivatives, benzothiazoles, benzothiophene dioxides, benzamides, boron compounds, isothiazolinones, thiocyanates, quaternary ammonium compounds, A guanidines, iodine derivatives, phenols, methoxyacrylates, oxides, dithiocarbamates, nitriles, quinolones, and Ag-, Zn- or Cu-containing zeolites.

6. The fungicidal composition according to claim 1, wherein the iodine-containing fungicide is 3-iodo-2-propynyl butylcarbamate (IPBC).

7. The fungicidal composition according to claim 1, wherein the iodine-containing fungicide is diiodomethyl-p-tolylsulfone.

8. A polymeric product comprising a thermoplastic polymer and the fungicidal composition as claimed in claim 1.

9. The polymeric product as claimed in claim 8, further comprising at least one plasticizer and at least one thixotropic agent.

10. The polymeric product as claimed in claim 9, wherein the thixotropic agents are triglycerides of castor oil derivatives, triglycerides of ricinoleic acid, or triglycerides of hydrogenated ricinoleic acid (12-hydroxyoctadecanoic acid), their esters or their amides and also their salts.

11. The polymeric product as claimed in claim 8, wherein the thermoplastic polymer is polyvinyl chloride.

12. A process for preparing the polymeric product as claimed in claim 10, the process comprising mixing the fungicidal composition with, and Incorporating the fungicidal composition into the thermoplastic polymer.

13. A process to protect polymeric products against attack and destruction by microorganisms, the process comprising adding the composition according to claim 1 to a thermoplastic polymer composition.

14. A process for protecting polyvinyl chloride against attack and destruction by microorganisms, the process comprising adding the composition according to claim 1 to a polyvinyl composition.

* * * * *